United States Patent
Jenkins et al.

(10) Patent No.: US 10,455,318 B2
(45) Date of Patent: Oct. 22, 2019

(54) EARMUFF WITH ELECTROACOUSTIC SHOCK ABSORBER

(71) Applicant: Honeywell International Inc., Morris Plains, NJ (US)

(72) Inventors: John Jenkins, San Diego, CA (US); Neal Muggleton, Stevenage (GB); Viggo Henriksen, Trondheim (NO); May Wilson, Wokingham (GB)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/969,293

(22) Filed: May 2, 2018

(65) Prior Publication Data

US 2018/0324517 A1   Nov. 8, 2018

Related U.S. Application Data

(60) Provisional application No. 62/500,655, filed on May 3, 2017.

(51) Int. Cl.
*G10K 11/178* (2006.01)
*H04R 1/10* (2006.01)
(Continued)

(52) U.S. Cl.
CPC ............ *H04R 1/1083* (2013.01); *A61F 11/14* (2013.01); *H04R 1/1008* (2013.01);
(Continued)

(58) Field of Classification Search
CPC ..... G10K 2210/129; G10K 2210/1291; G01H 17/00; G01M 15/12
(Continued)

(56) References Cited

U.S. PATENT DOCUMENTS 4,088,849 A * 5/1978 Usami ................ H04R 5/027
                                                     379/430
5,367,459 A * 11/1994 Shtarkman .......... B60G 17/018
                                                     180/197
(Continued)

FOREIGN PATENT DOCUMENTS

EP    3399770 A1    11/2018

OTHER PUBLICATIONS

Europe Patent Application No. 18170461.0, Extended European Search Report, dated Sep. 3, 2018, 8 pages.

*Primary Examiner* — George C Monikang
(74) *Attorney, Agent, or Firm* — Wick Phillips Gould & Martin, LLP

(57) ABSTRACT

A hearing protection earmuff may be configured to dampen vibrations at an interface. Generally, the hearing protection earmuff may comprise two ear cups, a headband attached to and connecting the ear cups, one or more sensors, a processor, an electroacoustic shock absorber, and an electromagnetic controller. Typically, the electromagnetic controller may be associated with an electroacoustic shock absorber and may be configured to control the dampening of the electroacoustic shock absorber. The dampening of the electroacoustic shock absorber may occur as a smart fluid changes viscosity in response to a signal received from the electromagnetic controller. In some embodiments, the clamping force between the headband and the ear cup may be varied by the electroacoustic shock absorber to minimize the vibrational impact on the user's ears. In some embodiments, the electroacoustic shock absorber may control the compressibility of the seal cushion located on each ear cup.

20 Claims, 2 Drawing Sheets

(51) Int. Cl.
*A61F 11/14* (2006.01)
*H04R 29/00* (2006.01)

(52) U.S. Cl.
CPC ......... *H04R 1/1041* (2013.01); *H04R 29/001* (2013.01); *A61F 2011/145* (2013.01); *H04R 1/1066* (2013.01)

(58) Field of Classification Search
USPC ...................................... 381/71.1, 71.2, 71.6
See application file for complete search history.

(56) References Cited

U.S. PATENT DOCUMENTS

| | | |
|---|---|---|
| 2011/0311079 A1 | 12/2011 | Keady |
| 2012/0061893 A1* | 3/2012 | Hochberg ................. F03G 7/08 267/195 |
| 2015/0300443 A1* | 10/2015 | Saito ....................... F16F 9/535 188/267.2 |
| 2016/0118035 A1* | 4/2016 | Hyde ................... H04R 1/1083 381/71.6 |
| 2017/0040012 A1 | 2/2017 | Goldstein |

\* cited by examiner

EARMUFF WITH ELECTROACOUSTIC SHOCK ABSORBER

CROSS-REFERENCE TO RELATED APPLICATIONS

The present application claims priority to U.S. Provisional Patent Application Ser. No. 62/500,655 filed May 3, 2017 by John Jenkins, et al. and entitled "Earmuff with Electroacoustic Shock Absorber" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD

The present disclosure relates generally to hearing protection earmuffs, and more particularly, to hearing protection earmuffs comprising an electroacoustic shock absorber.

BACKGROUND

In industrial work environments, periodically and/or continuously generated noise (e.g. vibration), for example, from mechanical handling of machinery (e.g. drilling) and/or alarm speakers may be a common occurrence. Generally, at both low and high frequencies, this may be harmful to the workers' ears and may potentially cause vibration-induced hearing loss and/or hearing damage over short and/or prolonged exposure periods. The issue of potential hearing damage often arises in manufacturing and other industrial facilities, but may also arise in military settings, airport settings, entertainment settings, and various other environments that involve exposure to high levels of noise and/or vibration. Generally, hearing damage due to exposure to prolonged periods of vibration, especially at low frequencies, may go unnoticed in the short term, but may cause permanent damage to an individual's hearing in the long term. Thus, it may be especially important to safeguard the hearing of individuals (such as workers, employees, customers, etc.) against harmful and/or prolonged vibration exposure by implementing the use of hearing protection. Standard passive earmuffs and other such hearing protection devices typically focus exclusively on reducing passage of vibrations from the air into the user's ear (e.g. noise reduction rating). However, vibrations (such as those induced by sound waves contacting an earmuff surface) may also introduce another source of noise into the user's ear (e.g. despite wearing of protective earmuffs with high noise reduction rating) due to movement of the earmuff cup with respect to the headband of the earmuff, for example.

SUMMARY

In an embodiment, a hearing protection earmuff may comprise two ear cups; a headband attached to and connecting the ear cups; one or more sensor attached to at least one of the ear cups configured to detect vibrations; a processor configured to receive a sensor signal from the one or more sensor, and configured to generate a control signal based on the sensor signal; one or more electroacoustic shock absorber configured to dampen vibrations at an interface; and one or more electromagnetic controller configured to control the dampening of the electroacoustic shock absorber in response to the control signal from the processor by generating a magnetic field.

In an embodiment, a method for dampening conduction of vibration within an earmuff may comprise detecting vibrations by a sensor attached to an ear cup of the earmuff; sending a sensor signal to a processor from the sensor; generating a control signal by the processor to an electromagnetic controller attached to the ear cup; generating a magnetic field by the electromagnetic controller to control an electroacoustic shock absorber; and dampening the detected vibrations by the electroacoustic shock absorber.

In an embodiment, an ear cup for use in a hearing protection earmuff may comprise a wireguide configured to attach the ear cup to a headband; one or more sensor attached to the ear cup configured to detect vibrations; a processor configured to receive a sensor signal from the one or more sensor, and configured to generate a control signal based on the sensor signal; one or more electroacoustic shock absorber configured to dampen vibrations at an interface between the ear cup and the headband; and one or more electromagnetic controller configured to control the dampening of the electroacoustic shock absorber in response to the control signal from the processor by generating a magnetic field.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
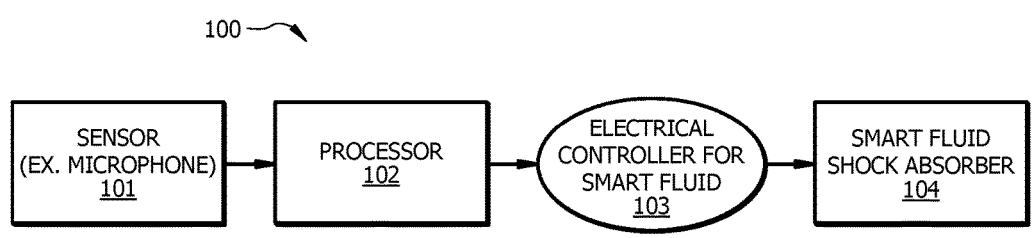
FIG. 1 is a schematic diagram illustrating an exemplary system for controlling an electroacoustic shock absorber of an exemplary earmuff.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Disclosed embodiments relate to systems and methods for providing hearing protection, including a hearing protection earmuff comprising an electroacoustic shock absorber (which may allow for the dampening level of the shock absorber to be electrically adjusted, for example to account for a detected vibration source which might introduce noise into the ear cup of the earmuff). Embodiments may also comprise a method for dampening vibrations within a hearing protection earmuff. To counteract the detected vibration source, thereby improving the hearing protection of such an earmuff and/or the ability of such an earmuff to reduce noise inside an earmuff (which for example, could be helpful in allowing a user to clearly hear transmitted sound within an ear cup of the earmuff, for example radio or other wireless communication transmitted via speaker into the ear cup), the hearing protection device (e.g. earmuff) of the present invention may comprise an electroacoustic shock absorber (for example, to dampen conduction of sound/noise/vibration from the interface of the ear cup and the headband of the earmuff).

Generally, one or more sensor (such as a microphone) might detect one or more vibration source, and the electroacoustic shock absorber might then be automatically adjusted accordingly (e.g. the dampening level of the electroacoustic shock absorber might be altered in response to the detected vibration source). This may result in a better earmuff, for example by minimizing conduction of sound into the ear cup, increasing the noise reduction rating (NRR) of the earmuff design, and/or changing (e.g. tuning) the resonance frequency of the ear cup.

In typical embodiments, the electroacoustic shock absorber may comprise magnetorheological fluid (MRF) (e.g. iron particles (such as carbonyl iron), cobalt particles, other metal particles, and/or alloy particles suspended in, for example, mineral oil, synthetic oil, water, glycol, etc.), operable to change viscosity based on/in response to a magnetic field. Such embodiments typically employ an electromagnetic controller to generate the magnetic field for controlling the viscosity/dampening of the electroacoustic shock absorber, generally in response to (or based on) a sensor signal from a sensor configured to detect relevant vibrations of the sort that might impact the ear cup and impart some noise to the ear cup. So, for example, disclosed hearing protection earmuff embodiments might comprise: two ear cups; a headband attached to and connecting the ear cups; a sensor (typically one for each ear cup); a processor; an electroacoustic shock absorber (typically one for/associated with each ear cup and) configured to dampen vibrations at an interface (e.g. between each ear cup and the headband); and an electromagnetic controller (typically one for/associated with each electroacoustic shock absorber and) configured to control the dampening level (e.g. viscosity) of the (corresponding) electroacoustic shock absorber. The sensor (s) of such embodiments might typically be configured to detect vibrations (e.g. sound, user movement, etc.) and transmit a sensor signal (indicative of such vibrations) to the processor. The processor would typically be configured to generate a control signal to the electromagnetic controller based on the sensor signal, while the electromagnetic controller would be configured to respond to the control signal by generating a magnetic field (based on the sensor signal and for interaction with the electroacoustic shock absorber). Typically, the electroacoustic shock absorber would comprise MRF operable to change viscosity based on/in response to a magnetic field (e.g. generated by the electromagnetic controller). Persons of skill should appreciate other types of electroacoustic shock absorbers configured to dampen vibrations. Generally, such electroacoustic shock absorber embodiments could be tuned/controlled/altered based on various types of vibrations to reduce negative vibrational impact to the earmuff (e.g. vibrations which might introduce noise into the ear cups of the earmuff) and, as a result, the user's hearing.

So, for example, if the vibrations being detected and accounted for are external sounds (which might, for example, induce vibrations in the ear cup relative to the headband), each sensor would typically comprise a microphone configured to detect (external) sound. Then, each electroacoustic shock absorber would typically be configured to dampen vibrations between the corresponding ear cup and the headband, and the processor would typically be configured to generate a control signal directing the electromagnetic controller to interact with the electroacoustic shock absorber (via magnetic field) to change the clamping force at the interface between the corresponding ear cup and the headband (for example, at a rate and an amplitude based on the sensor signal). In some embodiments, the sensor to detect movement/vibration may be located on an end of the headband closest to the ear cup. In some embodiments, there may be one or more sensors to detect movement. For example, in some embodiments, a first sensor may be located on the right end of the headband closest to the right ear cup, and a second sensor may be located on the left end of the headband closest to the left ear cup. By way of example, the viscosity of the electroacoustic shock absorber might be changed at a rate (e.g. frequency in Hz) identical to that of the sensor signal, and might decrease in proportion to any increase in amplitude based on the sensor signal. Generally, the electroacoustic shock absorber may adjust to have a lower viscosity to account for an increase in vibrations due to, for example, an increase in movement. Thus, the electroacoustic shock absorber could be adjusted to minimize any sound input into the ear cup from vibration transmission at the interface of the headband and the ear cup (e.g. dampening conduction of sound/noise/vibration from the interface of the headband to the ear cup) and/or to alter the resonance frequency of the corresponding ear cup. In some embodiments, each interface/electroacoustic shock absorber would comprise a wireguide connecting the corresponding ear cup to the headband, where movement might be imparted based on the viscosity of the surrounding smart fluid (e.g. MRF) in the electroacoustic shock absorber. In some embodiments, the sensor (for example, for each ear cup) might comprise a (one or more) microphone configured to detect external sounds. In some embodiments, an external microphone may be configured to detect external sound vibrations. For example, such a microphone could be located on an exterior of the ear cup.

Alternatively, the electroacoustic shock absorber might be controlled to compensate or minimize other types of noise/vibration sources. In other words, in addition to embodiments that account for external sound vibrations, other embodiments might account for speaker generated noise within an ear cup and/or vibrations due to movement of the user (e.g. movement vibrations imparted by contact of the earmuff with the user's head, at the headband and/or seal cushion of the ear cup). Thus, one or more vibration sources might be sensed (e.g. with a corresponding sensor configured to detect such vibration source), with the electroacoustic shock absorber then being adjusted to account for the one or more sensed vibrations, in order to minimize noise transmission (for example, noise conduction) into the ear cups of the earmuff.

In some embodiments, if the vibrations being sensed and accounted for are generated by a speaker within the ear cup, then the earmuff might further (or alternatively) comprise a speaker located (e.g. mounted) within (one or both) ear cup (for example, configured or operable to pass-through external sound, configured for communication (e.g., with other earmuffs), and/or configured for music or other entertainment projection into the ear). Then, the sensor (or perhaps a second sensor if the embodiment adjusts based on both external sound and speaker sound) (e.g., for each ear cup) might comprise a microphone configured to detect sound from the speaker. For example, such a microphone would generally be located (e.g. mounted) on the interior of the ear cup, to detect the speaker sound within the ear cup. Alternatively, the speaker vibrations might be detected using another sort of sensor (still configured to detect the speaker sound to be transmitted into the ear cup). For instance, the sensor (or perhaps a second sensor if embodiments adjust based on both external sound and speaker sound) (e.g., for each ear cup) could detect a speaker electrical signal, and translate that into a sensor signal indicative of the speaker sound output into the ear cup.

In another embodiment, the vibrations being sensed and accounted for may be generated by user movement. Typically, an internal microphone may detect resulting noise from user movement, and correlate (via a processor) (e.g. using pre-determined algorithms, etc.) the amount of user movement with the viscosity of the smart fluid in the shock absorber and/or seal cushion. In some embodiments, the sensor may measure the rotation of the headband with respect to the ear cup and/or longitudinal movement of the wireguide of the headband with respect to the ear cup connection and/or movement of the seal cushion of the ear cup with respect to the user's head. In some embodiments, the seal cushion of the ear cup may be filled with smart fluid, (e.g., MRF) and the smart fluid's viscosity may be manipulated to alter the compressibility/spring value of the seal cushion in a way that would be effective in minimizing noise transmission into the ear cup.

While persons of skill should understand the disclosed embodiments based on the above disclosure, the following figures may provide specific examples that may further clarify the disclosure.

Turning now to the drawings, FIG. 1 illustrates a schematic diagram of an exemplary system 100 for controlling an electroacoustic shock absorber of an exemplary earmuff. Typically, the components (of the system 100) involved in controlling the electroacoustic shock absorber may include at least one sensor (e.g. microphone) 101, a processor 102, an electrical controller 103, and a smart fluid 104. The one or more sensors 101 may typically be configured to detect vibrations (e.g. sound/user movement, etc.) and transmit a sensor signal (indicative of such vibrations) to the processor 102. Generally, the sensor 101 may be a microphone to detect external sounds and/or movement from the user. The processor 102 may typically be configured to receive one or more sensor signal from the one or more sensors 101 and may typically be configured to generate a control signal to the electrical (e.g. electromagnetic) controller 103 based on the sensor signal. Typically, the electrical controller 103 may be configured to respond to the control signal by generating a magnetic field to interact with the smart fluid of the electroacoustic shock absorber 104 (e.g., wherein the magnetic field would be generated in response to the control signal, which is indicative of/related to the sensor signal regarding vibrations). The electrical controller 103 may comprise an electromagnet. Typically, the smart fluid may comprise MRF operable to change viscosity based on/in response to the applied magnetic field. For example, if the amplitude of the sensor signal is high (e.g. more vibration is occurring), then the viscosity of the smart fluid may decrease (e.g. to reduce the amount of sound transmitted through the smart fluid). On the contrary, if the amplitude of the sensor signal is low (e.g. less vibration is occurring), then the viscosity of the smart fluid may increase (e.g. to increase the amount of sound transmitted through the smart fluid).

In some instances, the amount of viscosity may change over the course of vibrations, for example a high sensor signal might initially cause a decrease in viscosity of the smart fluid (e.g. to reduce sound transmission) but if the amplitude is sufficiently large that there is a risk of bottoming-out of the shock absorber, then the viscosity might be increased as the shock absorber approaches the bottom-out situation. Generally, the amount of noise/sound transmitted to the user's ears may depend on the NRR of the earmuff. In other words, the amount of noise/sound transmitted to the user's ears may be adjusted to achieve a specific NRR. Conceptually, in some embodiments, the electroacoustic shock absorber 104 may be tuned/controlled/altered based on various types of vibrations which might introduce noise into the ear cups of the earmuff.

Figure 2:
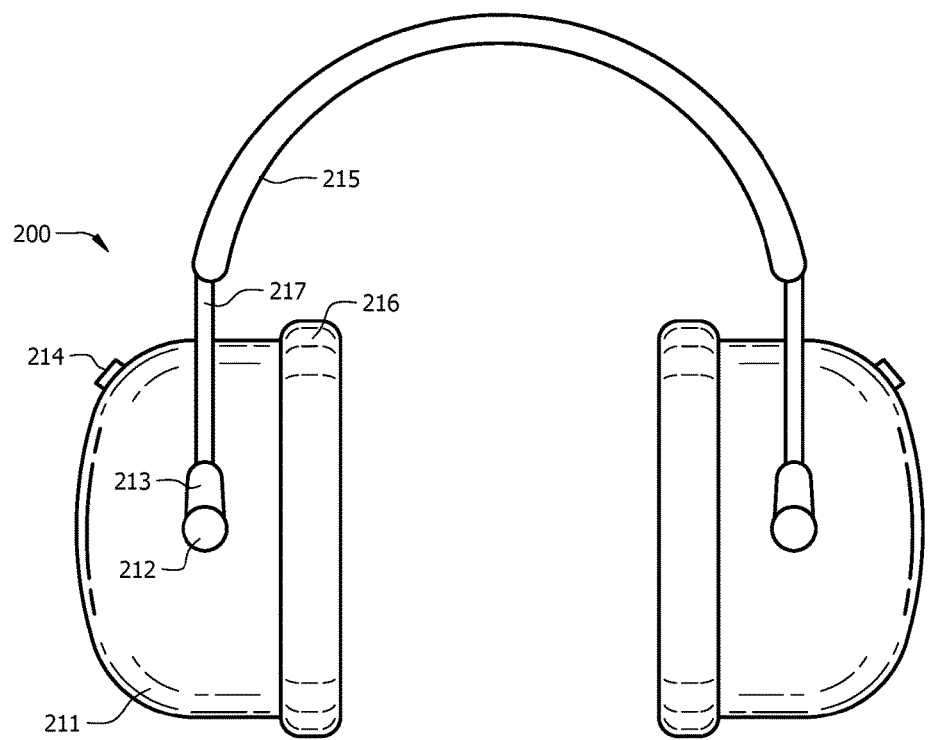
FIG. 2 illustrates a side view of an exemplary embodiment of an earmuff comprising an electroacoustic shock absorber.

FIG. 2 illustrates a side view of an exemplary embodiment of an earmuff 200 comprising one or more ear cups 211, a headband 215 configured to connect the ear cups 211, a microphone 214, an electroacoustic shock absorber 213, a seal cushion 216, and a wireguide 217. In some embodiments, the earmuff 200 may comprise two ear cups 211, for example a left ear cup and a right ear cup, configured to cover both of the user's ears. In some embodiments, the left ear cup and the right ear cup may comprise the same elements, while in other embodiments, the left ear cup and the right ear cup may comprise different elements. In the exemplary embodiment of FIG. 2, the microphone 214 is located on the exterior of the ear cup 211 to detect external sounds. Typically, the microphone 214 of the electroacoustic shock absorber 213 may interact with the processor, the electrical controller, and the smart fluid 212 in a manner similar to that described in reference to FIG. 1. Additionally, the electroacoustic shock absorber 213 may typically be configured to dampen the vibrations occurring between the ear cup 211 and the headband 215. The processor may typically be configured to generate a control signal directing the electromagnetic controller to interact with the electroacoustic shock absorber 213 (via magnetic field) to change the clamping force at the interface between the headband 215 and the ear cup 211. For example, the viscosity of the smart fluid 212 of the electroacoustic shock absorber 213 might change at a rate (e.g. frequency in Hz) identical to that of the sensor signal, and/or might decrease in proportion to any increase in amplitude based on the sensor signal. Thus, the electroacoustic shock absorber 213 may be adjusted to minimize any sound input (e.g. vibrational transmission) into the ear cup 211 by controlling the clamping force at the interface between the headband 215 and the ear cup 211. Generally, the clamping force may vary as the viscosity of the smart fluid 212 changes. In some embodiments, each interface/electroacoustic shock absorber 213 may comprise a wireguide 217 connecting the corresponding ear cup 211 to the headband 215, where movement may be imparted based on the viscosity of the surrounding smart fluid 212 (e.g. MRF) in the electroacoustic shock absorber 213.

Figure 3:
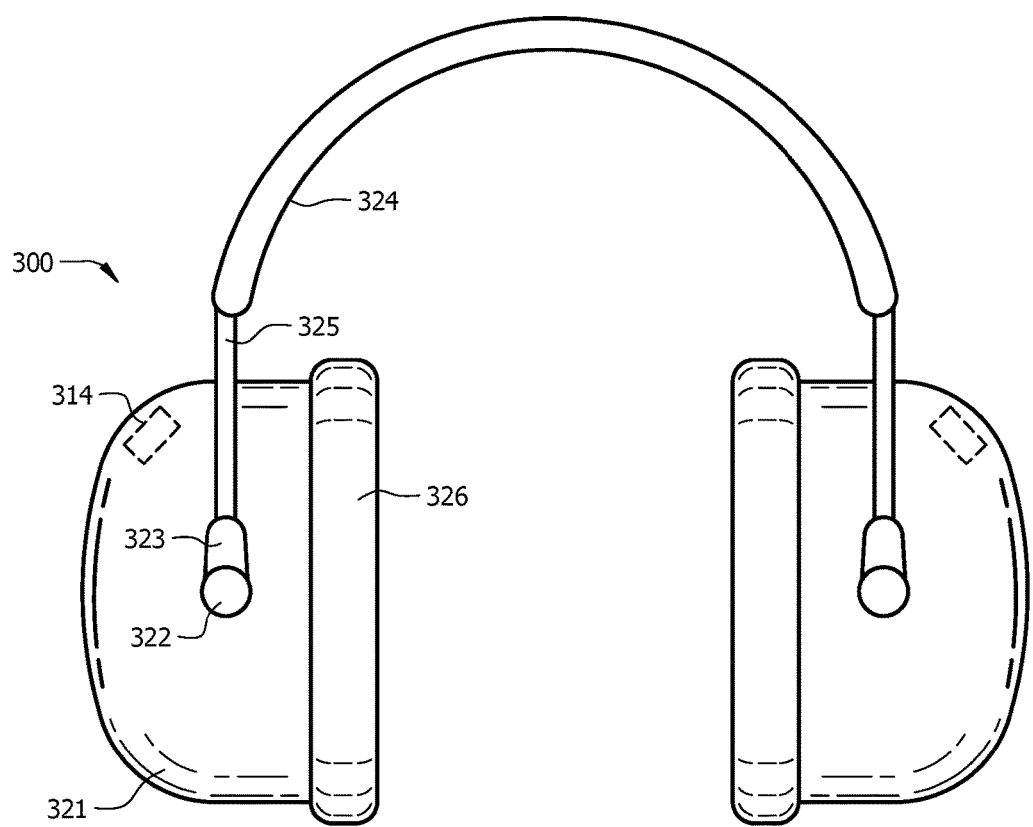
FIG. 3 illustrates another side view of an exemplary embodiment of an earmuff comprising an electroacoustic shock absorber.

FIG. 3 illustrates an alternative side view of an exemplary embodiment of an earmuff 300 comprising one or more ear cups 321, a seal cushion 326, a headband 324 configured to connect the ear cups 321, a wireguide 325, and an electroacoustic shock absorber 323. In some embodiments, the electroacoustic shock absorber 323 may account for speaker generated noise within an ear cup 321 and/or vibrations due to movement of the user. Typically, movement/vibration may be imparted by contact of the earmuff 300 with the user's head at the headband 324 and/or seal cushion 326 of the ear cup 321. Thus, one or more vibration sources might be sensed, with the electroacoustic shock absorber 323 then being adjusted to account for the one or more sensed vibrations in order to minimize noise transmission into the ear cups 321 of the earmuffs 300.

In the exemplary embodiment of FIG. 3, the vibrations being sensed and accounted for may be generated by user movement. Typically, an internal microphone 314 may detect resulting noise from user movement, and correlate (via a processor) (e.g. using pre-determined algorithms, etc.) the amount of user movement with the viscosity of the smart fluid 322 in the shock absorber. In some embodiments, the sensor may measure the rotation of the headband 324 with respect to the ear cup 321 and/or longitudinal movement of the wireguide 325 of the headband 324 with respect to the ear cup 321 connection and/or movement of the seal cushion of the ear cup 321 with respect to the user's head. In some embodiments, the seal cushion 326 of the ear cup 321 may be filled with smart fluid 322, and the smart fluid's 322 viscosity may be manipulated to alter the compressibility/ spring value of the seal cushion 326 in a way that would be effective in minimizing noise transmission into the ear cup 321.

The exemplary embodiment of FIG. 3 may sense vibration occurring due to noise being transmitted by a speaker. The speaker may be located (e.g. mounted) within (one or both) ear cup 321 (for example, configured or operable to pass-through external sound, configured for communication (e.g. with other earmuffs), and/or configured for music or other entertainment projection into the ear). Then, the sensor (or perhaps a second sensor if the embodiment adjusts based on both external sound and speaker sound) (for each ear cup 321) might comprise a microphone configured to detect sound from the speaker. For example, such a microphone would generally be located (e.g. mounted) on the interior of the ear cup 321, to detect the speaker sound within the ear cup 321. Alternatively, the speaker vibrations might be detected using another sort of sensor (still configured to detect the speaker sound to be transmitted into the ear cup 321). For instance, the sensor (or perhaps a second sensor if embodiments adjust based on both external sound and speaker sound) (for each ear cup 321) could detect a speaker electrical signal, and translate that into a sensor signal indicative of the speaker sound output into the ear cup 321.

Having described various devices and methods herein, exemplary embodiments or aspects can include, but are not limited to:

In a first embodiment, a hearing protection earmuff may comprise two ear cups; a headband attached to and connecting the ear cups; one or more sensor attached to at least one of the ear cups configured to detect vibrations; a processor configured to receive a sensor signal from the one or more sensor, and configured to generate a control signal (e.g. to an electromagnetic controller) based on the sensor signal (e.g. indication of/responsive to the detected vibrations); one or more electroacoustic shock absorber configured to dampen vibrations at an interface (e.g., of the ear cup with a headband, e.g., at a wireguide); and one or more electromagnetic controller configured to control the dampening of the electroacoustic shock absorber in response to the control signal from the processor by generating a magnetic field (wherein the magnetic field adjusts the viscosity of the electromagnetic shock absorber).

A second embodiment can include the hearing protection earmuff of the first embodiment, wherein the electroacoustic shock absorber comprises magnetorheological fluid configured to change viscosity in response to a magnetic field.

A third embodiment can include the hearing protection earmuff of the first or second embodiment, wherein the processor is configured to generate the control signal directing the electromagnetic controller to interact with the electroacoustic shock absorber to change the clamping force at the interface at a rate and an amplitude based on the sensor signal.

A fourth embodiment can include the hearing protection earmuff of any of the first through third embodiments, wherein the viscosity of the electroacoustic shock absorber is changed at a rate identical to that of the sensor signal and decreases in proportion to any increase in amplitude based on the sensor signal.

A fifth embodiment can include the hearing protection earmuff of the fourth embodiment, wherein the viscosity of the electroacoustic shock absorber is adjusted to alter the resonance frequency of the corresponding ear cup.

A sixth embodiment can include the hearing protection earmuff of any of the first through fifth embodiments, wherein the sensor comprises one or more microphone configured to detect external sound.

A seventh embodiment can include the hearing protection earmuff of any of the first through sixth embodiments, further comprising a speaker located within at least one ear cup, wherein the sensor comprises a microphone configured to detect sound from the speaker.

An eighth embodiment can include the hearing protection earmuff of any of the first through seventh embodiments, wherein the sensor detects vibrations arising from movement of a user of the earmuff.

A ninth embodiment can include the hearing protection earmuff of any of the first through eighth embodiments, wherein the interface is between the ear cup and the headband.

A tenth embodiment can include the hearing protection earmuff of the ninth embodiment, wherein the electroacoustic shock absorber is located in a wireguide attachment of the headband to the ear cup.

An eleventh embodiment can include the hearing protection earmuff of any of the first through tenth embodiments, wherein each ear cup further comprises a seal cushion, and wherein the interface is between the seal cushion of each ear cup and the head of the user.

A twelfth embodiment can include the hearing protection earmuff of the eleventh embodiment, wherein the electroacoustic shock absorber is located within the seal cushion.

In a thirteenth embodiment, a method for dampening conduction of vibration within an earmuff may comprise detecting vibrations by a sensor attached to an ear cup of the earmuff; sending a sensor signal to a processor from the sensor; generating a control signal by the processor to an electromagnetic controller attached to the ear cup; generating a magnetic field by the electromagnetic controller to control an electroacoustic shock absorber; and dampening the detected vibrations by the electroacoustic shock absorber.

A fourteenth embodiment can include the method of the thirteenth embodiment, wherein dampening the vibrations comprises dampening vibrations between the ear cup and a headband of the ear muff.

A fifteenth embodiment can include the gas detector of the thirteenth or fourteenth embodiment, wherein detecting vibrations by the sensor comprises detecting sounds external to the ear cup, and wherein the sensor comprises a microphone.

A sixteenth embodiment can include the gas detector of any of the thirteenth through fifteenth embodiments, wherein detecting vibrations by the sensor comprises detecting sounds within the ear cup, and wherein the sensor comprises a microphone.

A seventeenth embodiment can include the gas detector of any of the thirteenth through sixteenth embodiments, wherein dampening the detected vibrations by the electroacoustic shock absorber comprises changing the viscosity of the electroacoustic shock absorber (e.g. where the electroacoustic shock absorber comprises smart fluid, such as MRF).

In an eighteenth embodiment, (similar to the first embodiment above, but for example described with respect to only a single ear cup) an ear cup for use in a hearing protection earmuff may comprise a wireguide configured to attach the ear cup to a headband; one or more sensor attached to the ear cup configured to detect vibrations; a processor configured to receive a sensor signal from the one or more sensor, and configured to generate a control signal based on the sensor signal; one or more electroacoustic shock absorber configured to dampen vibrations at an interface between the ear cup and the headband (e.g., comprising MRF); and one or more electromagnetic controller configured to control the dampening of the electroacoustic shock absorber in response to the control signal from the processor by generating a magnetic field.

A nineteenth embodiment can include the ear cup of the eighteenth embodiment, wherein the sensor comprises a microphone attached to the exterior of the ear cup configured to detect external sounds.

A twentieth embodiment can include the ear cup of the eighteenth or nineteenth embodiment, further comprising a speaker positioned within the ear cup, wherein the sensor comprises a microphone attached to the interior of the ear cup configured to detect sounds from the speaker.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A hearing protection earmuff comprising:
   two ear cups;
   a headband attached to and connecting the ear cups;
   one or more sensor attached to at least one of the ear cups configured to detect vibrations at an interface;
   a processor configured to receive a sensor signal from the one or more sensor, and configured to generate a control signal based on the sensor signal;
   one or more electroacoustic shock absorber configured to dampen vibrations at the interface; and
   one or more electromagnetic controller configured to control dampening of the vibrations at the interface via the electroacoustic shock absorber in response to the control signal from the processor by generating a magnetic field;
   wherein the interface is between the ear cup and the headband or between a seal cushion of the ear cup and a head of a user.

2. The earmuff of claim 1, wherein the electroacoustic shock absorber comprises magnetorheological fluid configured to change viscosity in response to a magnetic field.

3. The earmuff of claim 1, wherein the processor is configured to generate the control signal directing the electromagnetic controller to interact with the electroacoustic shock absorber to change the clamping force at the interface at a rate and an amplitude based on the sensor signal.

4. The earmuff of claim 1, wherein the viscosity of the electroacoustic shock absorber is changed at a rate identical to that of the sensor signal and decreases in proportion to any increase in amplitude based on the sensor signal.

5. The earmuff of claim 4, wherein the viscosity of the electroacoustic shock absorber is adjusted to alter the resonance frequency of the corresponding ear cup.

6. The earmuff of claim 1, wherein the sensor comprises one or more microphone configured to detect external sound.

7. The earmuff of claim 1, further comprising a speaker located within at least one ear cup, wherein the sensor comprises a microphone configured to detect sound from the speaker.

8. The earmuff of claim 1, wherein the sensor detects vibrations arising from movement of a user of the earmuff.

9. The method of claim 1, wherein the electroacoustic shock absorber is located with the seal cushion of the ear cup and dampening the vibrations comprises dampening vibrations between the seal cushion of the ear cup and the head of the user by changing the viscosity of the electroacoustic shock absorber.

10. The earmuff of claim 1, wherein the electroacoustic shock absorber is located in a wireguide attachment of the headband to the ear cup.

11. The method of claim 1, wherein the electroacoustic shock absorber comprises magnetorheological fluid configured to change viscosity in response to the magnetic field.

12. The earmuff of claim 1, wherein the electroacoustic shock absorber is located within the seal cushion.

13. A method for dampening conduction of vibration within an earmuff, the method comprising:
   detecting vibrations at an interface by a sensor attached to an ear cup of the earmuff;
   sending a sensor signal to a processor from the sensor;
   generating a control signal by the processor to an electromagnetic controller attached to the ear cup;
   generating a magnetic field by the electromagnetic controller to control an electroacoustic shock absorber configured to dampen vibrations at the interface; and
   dampening the detected vibrations at the interface by the electroacoustic shock absorber;
   wherein the interface is between the ear cup and the headband or between a seal cushion of the ear cup and a head of a user.

14. The method of claim 13, wherein dampening the vibrations comprises dampening vibrations between the ear cup and a headband of the ear muff.

15. The method of claim 13, wherein detecting vibrations by the sensor comprises detecting sounds external to the ear cup, and wherein the sensor comprises a microphone.

16. The method of claim 13, wherein detecting vibrations by the sensor comprises detecting sounds within the ear cup, and wherein the sensor comprises a microphone.

17. The method of claim 13, wherein dampening the detected vibrations by the electroacoustic shock absorber comprises changing the viscosity of the electroacoustic shock absorber.

18. An ear cup for use in a hearing protection earmuff comprising:
   a wireguide configured to attach the ear cup to a headband;
   one or more sensor attached to the ear cup configured to detect vibrations at the wireguide;
   a processor configured to receive a sensor signal from the one or more sensor, and configured to generate a control signal based on the sensor signal;
   one or more electroacoustic shock absorber configured to dampen vibrations at the wireguide; and
   one or more electromagnetic controller configured to control dampening of the electroacoustic shock absorber in response to the control signal from the processor by generating a magnetic field.

19. The ear cup of claim 18, wherein the sensor comprises a microphone attached to the exterior of the ear cup configured to detect external sounds.

20. The ear cup of claim 18, further comprising a speaker positioned within the ear cup, wherein the sensor comprises a microphone attached to the interior of the ear cup configured to detect sounds from the speaker.

* * * * *